US00PP14886P2

(12) United States Plant Patent
Utecht

(10) Patent No.: US PP14,886 P2
(45) Date of Patent: Jun. 8, 2004

(54) GERANIUM PLANT NAMED 'FISROHOT'

(50) Latin Name: *Pelargonium zonale L'Héritier*
Varietal Denomination: Fisrohot

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,426

(22) Filed: Nov. 19, 2003

(30) Foreign Application Priority Data

Dec. 19, 2002 (CA) ..... PBR 02-3408

(51) Int. Cl.[7] ..... A01H 5/00

(52) U.S. Cl. ..... Plt./329

(58) Field of Search ..... Plt./329, 325

*Primary Examiner*—Kent Bell
(74) *Attorney, Agent, or Firm*—Foley & Lardner LLP

(57) ABSTRACT

A new and distinct cultivar of geranium plant named 'Fisrohot', particularly characterized by the combined features of brilliant purple with white, semi-double flowers, long strong peduncles, large, medium-green leaves with weak zonation, tall, but tight and well-branched plant habit, and medium late flowering response.

1 Drawing Sheet

Genus and species of the plant claimed: Hybrid of: *Pelargonium zonale* L'Héritier.
Variety denomination: 'Fisrohot'.

BACKGROUND OF THE INVENTION

The present invention comprises a new and distinct cultivar of geranium, botanically known as *Pelargonium zonale*, and hereinafter referred to by the cultivar name 'Fisrohot'.

'Fisrohot' is a product of a planned breeding program which had the objective of creating new zonal geranium cultivars with semi-double flowers, relatively vigorous, but well-branched growth habit, good outdoor performance, and in various flower colors.

'Fisrohot' originated from a hybridization made by the inventor, Angelika Utecht, in a controlled breeding program in Hillscheid, Germany, in 1998. The female parent was an unpatented hybrid seedling, no. 97-2191-1, with large, violet, semi-double flowers, dark green foliage with only slight zonation, and medium to vigorous growth habit. The male parent of 'Fisrohot' was the unpatented hybrid seedling No. 97-2001-3, which was derived from self-pollinating variety 'Fislypso' (U.S. Plant Pat. no. 11,162), and characterized by deep violet, semi-double flowers, medium to light green foliage without zonation, and low plant habit.

'Fisrohot' was selected as one flowering plant within the progeny of the stated cross by Angelika Utecht in 1999 in a controlled environment in Moncarapacho, Portugal.

The first act of asexual reproduction of 'Fisrohot' was accomplished when vegetative cuttings were taken from the initial selection in the fall of 1999, in a controlled environment in Moncarapacho, Portugal, by, or under the supervision of, Angelika Utecht.

Horticultural examination of plants grown from cuttings of the plant initiated in May 2000, in Hillscheid, Federal Republic of Germany, and continuing thereafter, has demonstrated that the combination of characteristics as herein disclosed for 'Fisrohot' are firmly fixed and are retained through successive generations of asexual reproduction.

'Fisrohot' has not been observed under all possible environmental conditions. The phenotype may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice. The following traits have been repeatedly observed and are determined to be basic characteristics of 'Fisrohot' in combination distinguish this geranium as a new and distinct cultivar:

1. Brilliant purple-violet flowers with small, white eyes;
2. Large, round inflorescences, long strong peduncles;
3. Large, medium-green leaves, with weak zonation;
4. Vigorous growth, tall and well-branched plant habit; and
5. Medium to late spring flowering response.

Of the many commercial cultivars known to the present inventor, the most similar in comparison to 'Fisrohot' are the varieties 'Fip 750' (U.S. Plant Pat. No. 14,011), and 'Fisrovio' (U.S. Plant Pat. No. 13,250).

In comparison to 'Fip 750', 'Fisrohot' has a similar main flower color, but medium-green, instead of dark-green, foliage, a much taller plant habit, and later begin of flowering.

In comparison to 'Fisrovio', flowers of 'Fisrohot' have a somewhat more bluish hue, they lack the orange eyes on petals, but show white bases instead, the zonation on leaves is somewhat more distinct, and internodes of branches are longer.

BRIEF DESCRIPTION OF THE DRAWING

The accompanying photographic drawing shows typical flower and foliage characteristics of 'Fisrohot' with colors being as true as possible with an illustration of this type. The photographic drawing shows a flowering potted 'Fisrohot' plant.

DETAILED BOTANICAL DESCRIPTION

The measurements were take in Hillscheid, Germany, in mid May 2003, 11 weeks after planting of rooted cuttings. The plants were growing in 14 cm pots, they had not been pinched. In the following description color references are made to The Royal Horticultural Society Color Chart. The color values were determined indoors from plants growing in a green-house in May 2003 in Hillscheid, Germany.

INFLORESCENCE

Umbel:

*Shape.*—Semi-spherical to nearly spherical.

*Average diameter.*—117 mm.

*Average depth.*—65–70 mm.

*Peduncle.*—233 mm in length, 4–4.5 mm in diameter.

*Peduncle color.*—Light green, RHS 143 C, one side may show a tinge of brown RHS 173 A.

*Pedicel.*—31 mm in length.

*Pedicel color.*—Light green, RHS 143 B, partly brownish infused, RHS 179 A.

*Number of flowers per umbel.*—About 45–65.

Corolla:

*Average diameter.*—53 mm.

*Form.*—Semi-double type.

*Shape.*—Round outline, flat cup-shape, with the upper petals about the same size as the lower petals.

*Number of petals.*—Approximately 7–9.

*Number of petaloids.*—None.

*Shape of petals.*—Obovate, base acute, upper end is truncate or rounded, margin is entire or very weakly crenated, and often wavy.

*Size of petals.*—Upper petals: 26–27 mm long, 21–23 mm wide; lower petals: 25–26 mm long, 22–23 mm wide.

*Color (general tonality from a distance of three meters).*—Bright violet purple.

*Color of upper petals.*—Main part between RHS N74 A and 74 B.

*Markings of upper petals.*—White bases more then a third of the petal, with fine pink veins RHS 68 B.

*Color of lower petals.*—RHS 74 B, uniform.

*Markings of lower petals.*—None.

*Color of lower surface of petals.*—RHS 67 B.

*Color of sepals.*—Outer surface: light green, RHS 144 A; inner surface: light green, RHS 144 B.

*Number of sepals.*—5.

*Shape of sepals.*—Linear to lanceolate, acute tip, truncate base, surface with moderate pubescence, margin entire.

*Size of sepals.*—12–14 mm long, 4 mm wide for the largest upper sepal, 2–3 mm in width for the other sepals.

Bud: (just prior to petals unfolding):

*Shape.*—Elliptical.

*Color of sepals.*—Light green, RHS 143 C.

*Color of petals.*—RHS 68 B.

*Length.*—20–21 mm.

*Width.*—12–13 mm.

Reproductive organs:

*Androecium.*—5–7 fertile anthers, plenty pollen, yellow-orange, RHS 26 A, filaments white, RHS 155 D, to light-pink, RHS 52 D.

*Gynoecium.*—One pistil, whitish style, RHS 155 D to 65 D, stigma 5–6-lobed stigma, dark-red, RHS 53 A.

*Fertility/seed seed.*—No seed set observed.

Spring flowering response period: In Hillscheid, Germany, in 2001 plants had on average 0.3 flowers opened 8 weeks after planting of rooted cuttings.

Outdoor flower production: Continuously and rich flowering, the flower count in 2003, in Hillscheid, Germany, indicated about 1–2 inflorescence per plant in mid May.

Durability: Good stability of flower color, good rain resistance.

Lastingness of the individual flower: About 8 days at 18° C., about 16 days for the umbel.

Fragrance: None.

PLANT

Foliage:

*Shape.*—Kidney-shaped, with cordate base, with the gap between the lowest lobes open, apex rounded with weak lobes.

*Margin.*—Bi-crenated.

*Texture.*—Upper surface smooth, dull.

*Size of leaf.*—115 mm wide, 75 mm long.

*Color of upper surface.*—Medium green, approximately RHS 137 C.

*Color of zonation.*—Brown, about RHS 166 A, distinctness weak to medium.

*Color of lower surface.*—RHS 143 B.

*Petioles.*—90 mm long, 2–2.5 mm diameter, green in color, approximately RHS 137 D.

General appearance and form:

*Stem color.*—Light green, RHS 143 C.

*Internode length.*—30–40 mm.

*Branching pattern.*—4–6 branches.

*Size of plants.*—20.3 cm tall, 37.1 cm wide, (11-week-old plants, as described, measured from the top of the soil (base of the main stem) to the surface of the foliage canopy, without inflorescences.

I claim:

1. A new and distinct cultivar of geranium plant named 'Fisrohot', as described and illustrated herein.

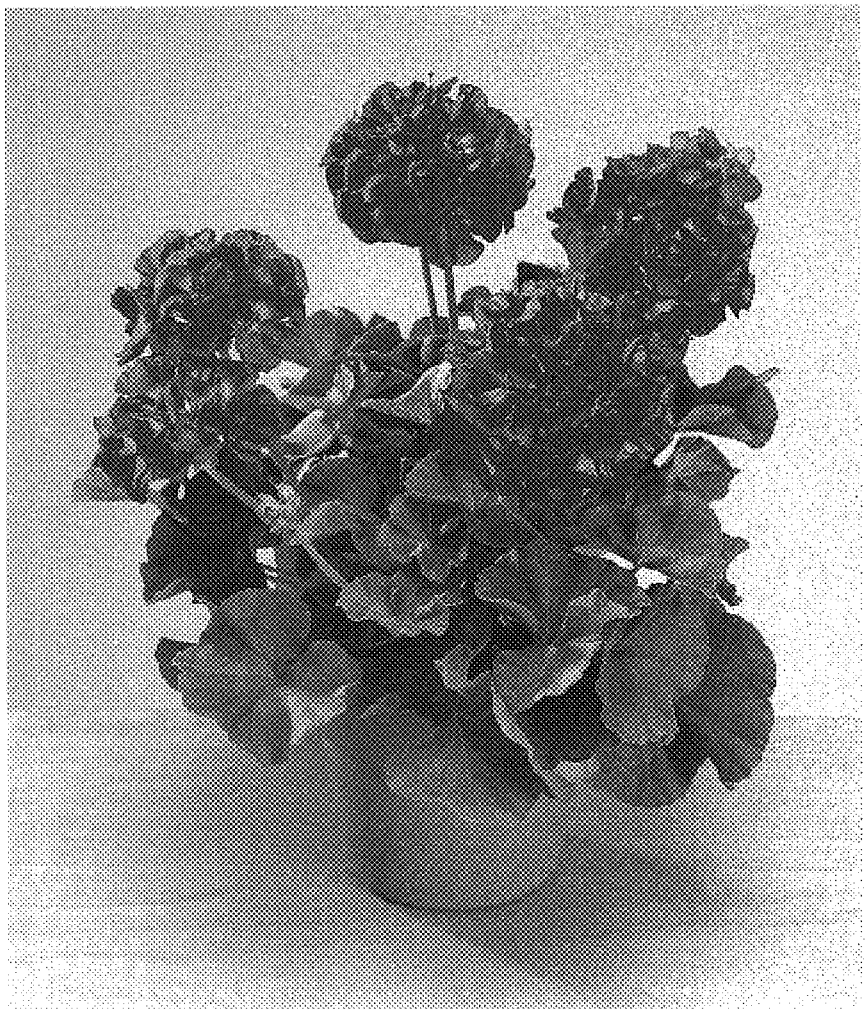

* * * * *